US007888406B2

(12) United States Patent
Yatake

(10) Patent No.: US 7,888,406 B2
(45) Date of Patent: Feb. 15, 2011

(54) SACCHARIDE-ALKYLENEOXY DERIVATIVE AND INK

(75) Inventor: Masahiro Yatake, Nagano-ken (JP)

(73) Assignee: Seiko Epson Corporation, Tokyo (JP)

( * ) Notice: Subject to any disclaimer, the term of this patent is extended or adjusted under 35 U.S.C. 154(b) by 371 days.

(21) Appl. No.: 11/903,649

(22) Filed: Sep. 24, 2007

(65) Prior Publication Data
US 2008/0163791 A1 Jul. 10, 2008

Related U.S. Application Data

(63) Continuation of application No. 09/909,417, filed on Jul. 19, 2001, now abandoned.

(30) Foreign Application Priority Data

Jul. 19, 2000 (JP) ............................. P2000-219459

(51) Int. Cl.
C09D 11/00 (2006.01)
(52) U.S. Cl. ...................................... 523/160; 523/161
(58) Field of Classification Search ................. 523/160, 523/161
See application file for complete search history.

(56) References Cited

U.S. PATENT DOCUMENTS

| 2,083,372 | A | 6/1937 | Guthmann | 134/29 |
|---|---|---|---|---|
| 3,291,580 | A | 12/1966 | Malick | 44/53 |
| 4,986,850 | A | 1/1991 | Iwata et al. | 106/25 |
| 5,034,423 | A | 7/1991 | Blount | 521/107 |
| 5,156,675 | A | 10/1992 | Breton et al. | 106/22 |
| 5,180,425 | A | 1/1993 | Matrick et al. | |
| 5,183,502 | A | 2/1993 | Meichsner et al. | 106/22 K |
| 5,196,056 | A | 3/1993 | Prasad | 106/15.05 |
| 5,356,464 | A | 10/1994 | Hickman et al. | |
| 5,503,664 | A | 4/1996 | Sano et al. | |
| 5,746,818 | A | 5/1998 | Yatake | |
| 5,948,155 | A | 9/1999 | Yui et al. | |
| 5,993,524 | A | 11/1999 | Nagai et al. | |
| 6,287,374 | B1 | 9/2001 | Yanagida et al. | |
| 6,432,186 | B1 | 8/2002 | Taniguchi | |
| 6,451,103 | B1 | 9/2002 | Uemura et al. | |
| 6,478,863 | B2 | 11/2002 | Johnson et al. | |
| 6,500,248 | B1 | 12/2002 | Hayashi | |
| 6,538,049 | B1 | 3/2003 | Kappele et al. | |
| 6,676,736 | B2 | 1/2004 | Nakano et al. | |
| 6,846,352 | B2 | 1/2005 | Yatake | |

FOREIGN PATENT DOCUMENTS

| DE | 19844004 | 3/2000 |
|---|---|---|
| EP | 0592774 | 4/1994 |
| EP | 978547 | 2/2002 |
| JP | 56147861 | 11/1981 |
| JP | 57-146720 | 9/1982 |
| JP | 59-59755 | 4/1984 |
| JP | 59059755 | 4/1984 |
| JP | 62-15269 | 1/1987 |
| JP | 62-15274 | 1/1987 |
| JP | 6215274 | 1/1987 |
| JP | 63-286291 | 11/1988 |
| JP | 3152170 | 6/1991 |
| JP | 418465 | 1/1992 |
| JP | 5-294880 | 11/1993 |
| JP | 05317676 | 12/1993 |
| JP | 9111165 | 4/1997 |
| JP | 9328644 | 12/1997 |
| JP | 11-343258 | 12/1999 |
| JP | 2000-44855 | 2/2000 |
| JP | 2000-169773 | 6/2000 |
| JP | 2000-169775 | 6/2000 |
| WO | 9309194 | 5/1993 |
| WO | 0022056 | 4/2000 |

OTHER PUBLICATIONS

English translation of JP 6-215274 dated Aug. 5, 1994.
Sperling, L.H. "Introduction to Physical Polymer Science" 2nd Edition John Wiley & Sons, NY (1992) pp. 97-99.
English translation of JP 62-15269 (1987).

Primary Examiner—Edward J Cain
(74) Attorney, Agent, or Firm—Ladas & Parry LLP

(57) ABSTRACT

A saccharide-alkyleneoxy derivative comprising a compound represented by the following formula (1):

$$A\text{-}(EP)n\text{-}OH \qquad (1)$$

wherein A represents a skeleton of a saccharide selected from the group consisting of $C_3$ to $C_{12}$ aldoses, ketoses and sugar alcohols; EP represents an ethyleneoxy group and/or a propyleneoxy group; and n represents an average number of the repeating units. Also disclosed are a method for producing the saccharide alkyleneoxy derivative, and an ink containing the saccharide-alkyleneoxy derivative.

18 Claims, No Drawings

SACCHARIDE-ALKYLENEOXY DERIVATIVE AND INK

This application is a continuation of application Ser. No. 09/909,417 filed on Jul. 19, 2001 now abandoned, claims the benefit thereof and incorporates the same by reference.

FIELD OF THE INVENTION

The present invention relates to a saccharide-alkyleneoxy derivative or a mixture thereof (hereinafter sometimes referred to as "a saccharide-alkyleneoxy derivative, etc"), a method for producing the same, and an ink containing the same. More particularly, the invention relates to an ink giving high printing quality to plain paper, regenerated paper or coated paper, and especially relates to an ink suitable for ink jet recording.

BACKGROUND OF THE INVENTION

Ink jet recording is a method of discharging ink from a fine nozzle as droplets to record letters or figures on a surface of a material to be recorded. As the ink jet recording system, there have come in practice a method of converting electric signals to mechanical signals by using an electrostrictive device to intermittently discharge ink stored in a nozzle head portion, thereby recording letters or figures on a surface of a material to be recorded, and a method of generating bubbles by rapidly heating ink stored in a nozzle head portion at a position quite close to a discharge portion to intermittently discharge the ink by cubical expansion due to the bubbles, thereby recording letters or figures on a surface of a material to be recorded.

Characteristics such as good drying of printing, no blur in printing, uniform printing on surfaces of all materials to be recorded and no mixing of colors in the case of multi-color printing have been required for the ink used in such ink jet printing. It particularly comes into question herein that blurs caused by fibers different in their permeability are liable to occur when paper is used as the material to be recorded.

Accordingly, various studies have hitherto been conducted for components of the ink. As means for decreasing the surface tension for that purpose, addition of diethylene glycol monobutyl ether as described in U.S. Pat. No. 5,156,675, addition of Surfynol 465 (manufactured by Nissin Chemical Industry Co., Ltd.), an acetylene glycol surfactant, as described in U.S. Pat. No. 5,183,502, and addition of both diethylene glycol monobutyl ether and Surfynol 465 have been studied. Diethylene glycol mono-n-butyl ether is described, for example, in U.S. Pat. No. 3,291,080. In the invention described in U.S. Pat. No. 2,083,372, it has been studied to use ethers of diethylene glycol in ink. As to the conventional ink for ink jet recording, polyglycerol is used as a detergent as described in JP-A-3-152170 (the term "JP-A" as used herein means an "unexamined published Japanese patent application"), or ethyleneoxy qroup-added polyglycerol is used as JP-A-9-328644, or ethyleneoxy group-added glycerin is used as described in JP-A-4-18465.

Further, as examples in which pigments are used, it has been studied and has come in practice that the surface tension is mainly maintained high (JP-A-4-18465) to inhibit the permeability, thereby inhibiting the wetting of ink on a surface of paper to secure printing quality, in many cases. Further, as combinations of glycol ethers and pigments, there are an example in which a pigment and triethylene glycol monomethyl ether are used as described in JP-A-56-148961, and an example in which an ether of ethylene glycol, diethylene glycol or triethylene glycol is used as described in JP-A-9-111165.

However, according to the conventional techniques, when the method of inhibiting the wetting of the ink on the surface of paper is used, the permeability of ink into paper is low, so that the ink runs on plain paper, particularly regenerated paper frequently used, and it takes a long time to dry printed matter. When continuously printed, therefore, sheets of printed paper cannot be stacked just after printing, because the ink on the printed paper is difficult to be dried. In addition, this method suffers from the problem that colors adjacent to each other are mixed to blur letters, in the case of multi-color printing.

The regenerated paper has various paper components mixed, and is a collection of components different in their rate of penetration, so that blurs are liable to occur by the difference in the rate of penetration between them. For decreasing the blurs, a process of heating paper has generally been studied. However, the heating of paper and other materials to be recorded in printing suffers from the problem that it takes a long time to elevate the temperature of a heating unit in a device to a predetermined temperature, that the consumption of electricity of a main body of a device is increased, or that paper and other materials to be recorded are damaged.

When ink containing a pigment is printed on paper having an ordinary sizing agent as a medium to be recorded, the problem is also encountered that the pigment remains on a surface of the paper unless permeability is imparted to some extent to the ink, thereby deteriorating scratch resistance. However, high surface tension limits the kind of paper for performing uniform printing, or is liable to cause deterioration of printing quality or image quality.

SUMMARY OF THE INVENTION

The present invention has been made to solve the foregoing problems.

Accordingly, an object of the present invention is to provide a novel additive for providing ink which is high in permeability into a medium to be recorded such as paper, is printable with few blurs on plain paper, particularly regenerated paper frequently used in recent years, without any heating means and generates no clogging.

Another object of the present invention is to provide an ink using the additive, particularly an ink for ink jet printing which is hard to clog a head tip of an ink jet printer.

Other objects and effects of the present invention will become apparent from the following description.

The novel compound useful as an additive to ink of the invention is a saccharide-alkyleneoxy derivative comprising a compound represented by the following formula (1):

A-(EP)n-OH    (1)

wherein A represents a skeleton of a saccharide selected from the group consisting of $C_3$ to $C_{12}$ aldoses, ketoses and sugar alcohols; EP represents an ethyleneoxy group and/or a propyleneoxy group; and n represents an average number of the repealing units. The saccharide-alkyleneoxy derivative of the invention may be a mixture of a plurality of compounds of formula (1).

In a preferred embodiment, the saccharide-alkyleneoxy derivative has an average number (n) of the repeating units in the above formula (1) being from 0.5 to 10.

The method for producing a saccharide-alkyleneoxy derivative represented by formula (1) below according to the invention comprises reacting at least one of ethylene oxide and propylene oxide with at least one saccharide selected from the group consisting of $C_3$ to $C_{12}$ aldoses, ketoses and sugar alcohols:

$$A\text{-}(EP)n\text{-}OH \quad (1)$$

wherein A represents a skeleton of a saccharide selected from the group consisting of $C_3$ to $C_{12}$ aldoses, ketoses and sugar alcohols; EP represents an ethyleneoxy group and/or a propyleneoxy group; and n represents an average number of the repeating units.

The ink of the invention is an ink containing at least a coloring material, water, and a saccharide-alkyleneoxy derivative comprising a compound represented by the following formula (1);

$$A\text{-}(EP)n\text{-}OH \quad (1)$$

wherein A represents a skeleton of a saccharide selected from the group consisting of $C_3$ to $C_{12}$ aldoses, ketoses and sugar alcohols; EP represents an ethyleneoxy group and/or a propyleneoxy group; and n represents an average number of the repeating units. As described above, the saccharide-alkyleneoxy derivative of the invention may be a mixture of a plurality of compounds of formula (1).

In a preferred embodiment of the ink according to the invention, the average number (n) of the repeating units in the saccharide-alkyleneoxy derivative represented by the above formula (1) is from 0.5 to 10.

In another preferred embodiment of the ink according to the invention, the ink contains one or more $C_3$ to $C_{12}$ saccharides selected from the group consisting of: aldoses having 6 or less carbon atoms, including glyceraldehyde, erythrose, threose, arabinose, xylose, glucose, mannose, talose and galactose; aldoses having from 7 to 12 carbon atoms; ketoses having 6 or less carbon atoms, including erythrulose, ribulose, xylulose, lactose, psicose, tagatose and sorbose; ketoses having from 7 to 12 carbon atoms; sugar alcohols having from 6 or less carbon atoms, including glycerol, erythritol, xylitol, sorbitol and mannitol; sugar alcohols having from 7 to 12 carbon atoms.

In a still other preferred embodiment of the ink according to the invention, the ink contains at least one substance represented by formula (2) below in an amount of 0% to 10% by weight:

$$R\text{-}(EP)m\text{-}OH \quad (2)$$

wherein R represents an alkyl group having from 4 to 10 carbon atoms, which may be branched, a cycloalkyl group or a phenyl group; EP represents an othyleneoxy group and/or a propyleneoxy group; and m represents an average number of the repeating units.

DETAILED DESCRIPTION OF THE INVENTION

The novel compound of the invention is the saccharide-alkyleneoxy derivative represented by the following formula (1) or a mixture thereof, and was newly found, when extensive studies had been made considering that ink and recorders using the same, particularly ink used for ink jet recording and ink jet recording apparatuses using the same, require characteristics such as good drying of printing, no blur in printing, uniform printing on surfaces of all materials to be recorded and no clogging in heads:

$$A\text{-}(EP)n\text{-}OH \quad (1)$$

wherein A represents a skeleton of a saccharide selected from the group consisting of $C_3$ to $C_{12}$ aldoses, ketoses and sugar alcohols; EP represents an ethyleneoxy qroup and/or a propyleneoxy group; and n represents an average number of the repeating units.

The saccharide-alkyleneoxy derivative represented by the above-mentioned formula (1) or a mixture thereof can also be used in writing ink, ink for lithography, stamp ink and ink ribbon ink, as well as in ink for ink jet recording.

Further, the saccharide-alkyleneoxy derivative represented by the above-mentioned formula (1) or a mixture thereof is high in safety to the human body, is a transparent, viscous liquid, has moisture-retaining properties, a high boiling point and a low freezing point. Accordingly, it can also be used as a humectant for cosmetics, an additive for research and experiments of animals and plants, an additive for attraction of insecticides or an antifreeze solution.

The saccharide-alkyleneoxy derivative represented by the above-mentioned formula (1) of the invention or a mixture thereof is produced by reacting ethylene oxide and/or propylene oxide with at least one saccharide selected from the group consisting of $C_3$ to $C_{12}$ aldoses, ketoses and sugar alcohols.

The saccharide-alkyleneoxy derivative is a substance produced by reacting ethylene oxide and/or propylene oxide with at least one saccharide selected from the group consisting of $C_3$ to $C_{12}$ aldoses, ketoses and sugar alcohols, and obtained as a mixture containing a group of substances having at least one ethylene oxide and/or propylene oxide combined with one saccharide.

The mixture of the saccharide-alkyleneoxy derivative(s) is a substance obtained by mixing two or more of the above-mentioned saccharide-alkyleneoxy derivatives, or a substance obtained by reacting ethylene oxide and/or propylene oxide with two or more saccharides selected from the above-mentioned three kinds of saccharides, and obtained as a mixture containing a group of substances having at least one ethylene oxide and/or propylene oxide combined with each of the two or more saccharides.

The average number (n) of repeating units can be easily adjusted by suitably selecting the reaction conditions such as the ratio of the saccharide to ethylene oxide and/or propylene oxide and the reaction temperature.

Further, the above-mentioned group of substances may include those different in the number of ethyleneoxy groups and/or propyleneoxy groups combined with one saccharide and the bonding position. In some cases, unreached saccharides are contained.

When ethylene oxide and/or propylene oxide is reacted with at least one saccharide selected from the above-mentioned three kinds of saccharides of $C_3$ to $C_{12}$ aldoses, ketoses and sugar alcohols, it is preferred that the reaction is conducted in the presence of a catalyst, preferably in the presence of an alkaline catalyst.

As the alkaline catalyst, there can be used an alkanolamine such as monoethanolamine, diethanolamine, triethanolamine or tripropanolaminc, an alkylalkanolamine such as methyldiethanolamine, ethyldiethanolamine, dimethylethanolamine or diethylethanolamine, an alkylamine such as trimethylamine, methyldiethylamine or dimethylethylamine, or an inorganic salt such as ammonia, urea, KOH, NaOH or LiOH.

The above-mentioned reaction is preferably conducted under an inert atmosphere.

Further, some of the above-mentioned saccharides are liable to discolor by the Maillard reaction, so that it is necessary to make them hard to discolor by using a saccharide hard to discolor, or by paying attention to the heating time and temperature or inert gas substitution.

The saccharide-alkyleneoxy derivative represented by the above-mentioned formula (1) or a mixture thereof in which the average number (n) of repeating units of the ethyleneoxy groups and/or the propyleneoxy groups is from 0.5 to 10 is preferred as an additive to ink, particularly ink for ink jet recording.

Then, in the following description, the case that the saccharide-alkyleneoxy derivative represented by the above-mentioned formula (1) or a mixture thereof is particularly used in ink for ink jet recording is described as a typical example in detail. Of course, it is to be understood that the use of the saccharide-alkyleneoxy derivative represented by the above-mentioned formula (1) or a mixture thereof is not limited to the ink for ink jet recording.

The ink of the invention is ink for ink jet recording containing at least a water-soluble coloring material and water, and has a feature or containing the saccharide-alkyleneoxy derivative represented by the above-mentioned formula (1) or a mixture thereof.

The average number (n) of the repeating units in the saccharide-alkyleneoxy derivative represented by the above-mentioned formula (1) or a mixture thereof is preferably from 0.5 to 10. When n is less than 0.5, the effect of addition thereof is low to cause low moisture retention. Clogging is therefore liable to occur. However, when it is used in combination with a saccharide described later, n is not limited thereto.

On the other hand, when n exceeds 10, the viscosity thereof unfavorably increases, so that the use thereof as the ink for ink jet recording becomes difficult.

It is preferred that the repeating unit (EP) in the saccharide-alkyleneoxy derivative represented by the above-mentioned formula (1) or a mixture thereof is an ethyleneoxy group and/or a propyleneoxy group and the saccharide-alkyleneoxy derivative or a mixture, thereof has a molecular weight distribution in ink. In particular, when low-viscosity ink is required, ethyleneoxy group-containing one is preferably used, and when high-viscosity ink is required, propyleneoxy group-containing one is preferably used. The amounts of these can be properly selected.

The ink containing the saccharide-alkyleneoxy derivative or a mixture thereof having a molecular weight distribution tends to approach the Newtonian fluid, which preferably improves the discharge stability of the ink. Although the weight average molecular weight (Mw)/number average molecular weight (Mn) is preferably 2 or more, it is to be understood that less than 2 is denied.

The number average molecular weight of the saccharide-alkyleneoxy derivative represented by the above-mentioned formula (1) or a mixture thereof is preferably 1000 or less. When the average molecular weight exceeds 1000, the "intermittent printing characteristic", the characteristic of discharging ink after no discharge for a definite time to conduct printing, is deteriorated.

Further, in the saccharide-alkyleneoxy derivative represented by the above-mentioned formula (1) or a mixture thereof, A represents a skeleton of a saccharide selected from the group consisting of $C_3$ to $C_{12}$ aldoses, ketoses and sugar alcohols, and particularly a skeleton of a saccharide selected from the group consisting of: aldoses having 6 or less carbon atoms, including glyceraldehyde, erythrose, threose, arabinose, xylose, glucose, mannose, talose and galactose; aldoses having from 7 to 12 carbon atoms; ketoses having 6 or less carbon atoms, including erythrulose, ribulose, xylulose, lactose, psicose, tagatose and sorbose; ketoses having from 7 to 12 carbon atoms; sugar alcohols having 6 or loss carbon atoms, including glycerol, erythritol, xylitol, sorbitol and mannitol; and sugar alcohols having from 7 to 12 carbon atoms. A skeleton having 2 or less carbon atoms is likely to evaporate at ordinary temperature, and does not have as high moisture retention ability as one having 3 or more carbon atoms. Accordingly, the effect of preventing clogging is low. However, it is to be understood that a skeleton having 2 or less carbon atoms is not denied. Further, a skeleton having 12 or less carbon atoms is preferred. A skeleton having 13 or more carbon atoms increases in viscosity, so that it becomes difficult to use as the ink for ink jet recording, although depending on the amount thereof added. However, a skeleton having 13 or more carbon atoms is not denied, and may be used in an amount of 20% or less.

The content of the saccharide-alkyleneoxy derivative represented by the above-mentioned formula (1) or a mixture thereof in the ink is preferably from 0.1% to 30% by weight.

Further, in the ink of the invention, the above-mentioned $C_3$ to $C_{12}$ saccharide can be used in combination with the saccharide-alkyleneoxy derivative represented by the above-mentioned formula (1) or a mixture thereof. In that case, the total amount of the saccharide alkyleneoxy derivative represented by the above-mentioned formula (1) or a mixture thereof and the above-mentioned $C_3$ to $C_{12}$ saccharide is preferably from 0.5% to 30% by weight. When the content thereof is less than 0.5% by weight, the effect of moisture retention is low, and therefore, clogging is liable to occur. On the other hand, when the content exceeds 30% by weight, the viscosity thereof unfavorably increases, so that the use thereof as the ink for ink jet recording becomes difficult. More preferably, the content is from 3% to 15% by weight. Specific examples of the saccharides used in combination with the saccharide-alkyleneoxy derivative represented by the above-mentioned formula (1) or a mixture thereof include general saccharides such as glyceraldehyde, erythrose, threose, arabinose, xylose, glucose, mannose, talose, erythrulose, ribulose, xylulose, lactose, psicose, tagatose, sorbose, glycerol, erythritol, xylitol, sorbitol, mannitol, trehalose, kojibiose, nigrose, maltose, isomaltose, isotrehalose, sophorose, laminaribiose, cellobiose, gentiobiose, N-acetylglucosamine, glucosamine, 3,6-anhydrogalactose, carboxymethyl cellulose, fractooligosaccharide, isomaltooligosaccharide, gentiooligosaccharide, straight-chain oligosaccharide, lactooligosaccharide, soybeanoligosaccharide, xylooligosaccharide, chitin-chitooanoligosaccharide, pectinoligosaccharide, agarooligosaccaharide, inulioligosaccharide, galactooligosaccharide, lactosucrose, lactulose, lactitol, paranichit, reduced glutinous starch syrup, pectin, gum arabic, cyamoposis gum, locust bean gum, carageenan, alginate, pullulan, xanthan gum, curdlan and polydextrose.

Further, the surface tension of the ink of the invention at 25° C. is preferably 40 mN/m or less. When the surface tension exceeds 40 mN/m, the permeability is lowered to cause time-consuming drying on a medium such as paper, or liability to the bleed phenomenon that colors are mixed in multi-color printing. The surface tension is more preferably from 28 mN/m to 35 mN/m.

Further, it is preferred that the ink of the invention contains di(tri)ethylene glycol monobutyl ether in an amount of 0% to 20% by weight, and (di)propylene glycol monobutyl ether in an amount of 0% to 10% by weight.

Still further, the ink of the invention preferably contains a 1,2-alkylene glycol having from 4 to 10 carbon atoms in an amount of 0% to 10% by weight. The addition of the 1,2-alkylene qlycol having from 4 to 10 carbon atoms can reduce blurs. In particular, 1,2-pentanediol and 1,2-hexanediol are preferred. The content thereof is preferably from 0% to 10% by weight, and when another permeating agent is contained, the content is 0%. Even when the content exceeds 10% by weight, the permeability is not more improved. Accordingly, the content is preferably up to 10% by weight for lowering the viscosity. The content is preferably from 3% to 10% by weight for 1,2-pentanediol, and from 0.5% to 5% by weight for 1,2-hexanediol.

Furthermore, the ink of the invention preferably contains an acetylene glycol surfactant in an amount of 0% to 5% by weight. The addition of the acetylene glycol surfactant can reduce blurs. In particular, Orfin E series (manufactured by Nissin Chemical Industry Co., Ltd.) and Surfynol series (manufactured by Nissin Chemical Industry Co., Ltd.) are preferred. The content thereof is from 0% to 5% by weight, and when another permeating agent is contained, the content is 0%. Even when the content exceeds 5% by weight, the permeability is not more improved. Accordingly, the content is preferably up to 5% by weight for lowering the viscosity. The content is more preferably from 0.5% to 2% by weight.

Moreover, the ink of the invention preferably contains a substance represented by the following formula (2) in an amount of 0% to 10% by weight:

$$R\text{-}(EP)_m\text{-}OH \qquad (2)$$

wherein R is preferably an alkyl group having from 4 to 10 carbon atoms, a cycloalkyl group or a phenyl group, and particularly preferably a branched alkyl group; EP is an ethyleneoxy group and/or a propyleneoxy group; and m is an average number of the repeating units.

The average number (m) of the substance represented by formula (2) existing in the ink system is at least 1, and preferably from 1 to 10. The average number (m) of propyleneoxy groups is 0.5 or more, and preferably from 0.5 to 5, when they exist. When another permeating agent is contained, the content of the substance represented by formula (2) is 0%. Even when the content exceeds 10% by weight, the permeability is not more improved. Accordingly, the content is preferably up to 10% by weight for lowering the viscosity. The content is more preferably from 0.5% to 6% by weight.

In addition, the coloring material used in the ink of the invention is a water-soluble dye and/or a water-soluble pigment that is made water-dispersible. Although dyes and pigments include water-soluble and oil-soluble ones, the water-soluble dye and/or pigment is preferred in the invention.

The pigments used in the invention can be made water-dispersible by surface oxidation and/or coating with polymers by known means.

Although the pigments include ones dispersed in water using dispersing agents composed of surfactants or polymers, ones made water-dispersible by surface oxidation, and ones made water-dispersible by coating with polymers, the surface-treated pigments and/or the pigments coated with polymers are preferred for ink jet printing from the viewpoints of discharge stability of ink and a decrease in viscosity. Further, the surface-treated pigments and/or the pigments coated with polymers withstand severer conditions than the pigments dispersed in water using dispersing agents, and are stable at lower temperatures and higher temperatures. They can therefore provide ink usable in a wide range. The ink of the invention is preferably ink used in an ink jet recording apparatus having a head discharging the ink by response of signals by use of an electrostrictive device. Methods for discharging ink by the ink jet system include a method using an electrostrictive device such as a piezoelectric element, and a method of generating bubbles by rapid heating to discharge ink by cubical expansion due to the bubbles. The ink of the invention is particularly effective when used in an ink jet recording apparatus having a head discharging the ink by response of signals by use of an electrostrictive device, and secures the prevention of clogging and discharge stability.

The ink of the invention can appropriately contain additives such as a preservative, an antioxidant, an electric conductivity regulating agent, a pH regulating agent, a viscosity regulating agent, a surface tension regulating agent and an oxygen absorber, as additional components.

For inhibiting the drying of the ink at the front of a nozzle, a water-soluble glycol is preferably added to the ink of the invention. Examples of such glycols include ethylene glycol, diethylene glycol, triethylene glycol, propylene glycol, dipropylene glycol, tripropylene glycol, polyethylene glycol having a molecular weight of 2000 or less, 1,3-propylene glycol, isopropylene glycol, isobutylene glycol, 1,4-butanediol, 1,3-butanediol, 1,2-pentanediol, 1,5-pentanediol, 1,2-hexanediol, 1,6-hexanediol, 1,2,6-hexanetriol, 1,8-octanediol, 1,2-octanediol, glycerol, mesoerythritol and pentaerythritol.

Further, the ink of the invention can also contain many kinds of saccharides for inhibiting clogging with the ink dried at the front of a nozzle. The saccharides include monosaccharides and polysaccharides, and there can be used alginic acid and salts thereof, cyclodextrins and celluloses, as well as glucose, mannose, fructose, ribose, xylose, arabinose, lactose, galactose, aldonic acid, glucitose, maltose, cellobiose, sucrose, trehalose and maltotriose.

Furthermore, the ink of the invention can contain other compounds having compatibility with water, improving the solubility of qlycol ethers and ink components having low solubility in water contained in the ink, further improving the permeability of the ink into a material to be recorded such as paper, or inhibiting the clogging of a nozzle. Such compounds include an alkyl alcohol having from 1 to 4 carbon atoms, a glycol ether (e.g., ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, diethylene glycol mono-n-butyl ether, triethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, propylene glycol mono-n-butyl ether, dipropylene glycol mono-n-butyl ether), formamide, acetamide, dimethyl sulfoxide, sorbit, sorbitan, acetin, diacetin, triacetin and sulfolane. They can be appropriately selected and added.

The ink of the invention can also contain other surfactants for further controlling the permeability. As the surfactants contained, preferred are surfactants compatible with the ink, which are shown in Examples described later. Of the surfactants, preferred are ones high in permeability and stable. Examples thereof include amphoteric surfactants and nonionic surfactants. The amphoteric surfactants include lauryldimethylaminoacetic acid betaine, 2-alkyl-N-carboxymethyl-N-hydroxy-ethylimidazolinium betaine, coconut fatty acid amidopropyldimethylaminoacetic acid betaine, polyoctyl-polyaminoethylglycine and other imidazoline derivatives. The nonionic surfactants include ethers such as polyoxyethylene nonyl phenyl ether, polyoxyethylene octyl phenyl ether, polyoxyethylene dodecyl phenyl ether, polyoxyethylene alkyl allyl phenyl ethers, polyoxyethylene oleyl ether, polyoxyethylene lauryl ether, polyoxyethylene alkyl ethers and polyoxyalkylene alkyl ethers; esters such as polyoxyethyleneoleic acid, polyoxyethylene oleate, polyoxyethylene distearate, sorbitan laurate, sorbitan monostearate, sorbitan monooleate, sorbitan sesquioleate, polyoxyethylene monooleate and polyoxyethylene stearate; and fluorine-containing surfactants such as fluorine alkyl esters and perfluoroalkyl carbonates.

Further, the ink of the invention can also contain, for example, sodium benzoate, sodium pentachlorophenolate, sodium 2-pyridinethiol-1-oxide, sodium sorbate, sodium dehydroacetate or 1,2 dibenzothiazoline-3-one (Proxel CRL, Proxel BDN, Proxel GXL, Proxel XL-2 and Proxel TH supplied from I.C.I), as a preservative or an antifungal agent.

The ink of the invention can also contain a pH regulating agent, a solubilizing agent or an antioxidant. Such agents include alkanolamines such as diethanolamine, triethanolamine and propanolamine, alkylalkanolamines such as methyldiethanolamine, dimethylethanolamine, ethyldiethanolamine and diethylethanolamine, and amines such as morpholino, and modified products thereof; inorganic salts such as potassium hydroxide, sodium hydroxide and lithium hydroxide; ammonium hydroxide; quaternary ammonium hydroxides (such as tetra-methylammonium); carbonates such as potassium carbonate, sodium carbonate and lithium carbonate; phosphates; urea derivatives such as N-methyl-2-pyrrolidone, urea, thiourea and tetramethylurea; allophanate compounds such as allophanates and methyl allophanate; biuret compounds such as biuret, dimethylbiuret and tetramethylbiuret; and L-ascorbic acid and salts thereof.

Furthermore, the ink of the invention can also contain a rosin, alginic acid, polyvinyl alcohol, hydroxypropyl cellulose, carboxymethyl cellulose, hydroxyethyl cellulose, methyl cellulose, a polyacrylate, polyvinylpyrrolidone or gum arable starch, as a viscosity regulating agent.

It is preferred that the ink of the invention is used in an ink jet recording apparatus having a head which discharges an ink by response due to an electrostrictive device. An ink jet recording apparatus of the system of heating a head portion thereof has the harmful influence that the coloring materials and other components contained in the ink are decomposed to result in liability to the clogging of the head. When the ink is used in the ink jet recording apparatus having a head discharging the ink by response due to an electrostrictive device, such a problem does not arise. Accordingly, the ink of the invention can be stably used.

When the solid matter such as a dye is used in a relatively large amount in the ink of the invention, the ink dries at the front of a nozzle through which the ink is not discharged for a long period of time to cause an increase in its viscosity. Accordingly, the phenomenon that printing is disturbed is liable to occur. However, the ink is stirred by slightly moving it at the front of the nozzle to such a degree that the ink is not discharged, and therefore, the ink can be stably discharged. This is easily controlled by use of an electrostrictive device. The method of rapidly heating the vicinity of the nozzle generates bubbles, so that such control is impossible. Accordingly, by using this mechanism and the ink of the invention, the concentration of the coloring material in the ink can be increased. When the coloring material is a pigment, even the use of a material which is easily foamed, such as an emulsion, makes it possible, to increase the color density and moreover to stably discharge the ink.

In the ink of the invention, when the coloring material Is a pigment, a water-soluble emulsion comprising fine polymer particles is preferably added.

The amount thereof added is from 1% to 10% by weight as the net amount of line polymer particles in the ink. Less than 1% by weight results in a decrease in the effect of improving abrasion resistance, whereas exceeding 10% by weight results an increase in viscosity of the ink, which makes it hard to use the ink as ink for ink jet recording.

Fine polymer particles A to D contained in the ink of the invention can be prepared as described below:

Fine Polymer Particles A:

In a reaction vessel equipped with a dropping equipment, a thermometer, a water cooled reflux condenser and a stirrer, 100 parts of ion-exchanged water is placed, and 0.2 part of potassium persulfate is added as a polymerization initiator in an atmosphere of nitrogen at 70° C. with stirring. A monomer solution obtained by adding 0.05 part of sodium laurylsulfate, 5 parts of styrene, 6 parts of tetrahydrofurfuryl acrylate, 5 parts of butyl methacrylate and 0.02 part of t-dodecylmercaptan to 7 parts of ion-exchanged water is added dropwise to the resulting aqueous solution at 70° C. to conduct reaction, thereby preparing a primary material. Then, 2 parts of a 10% solution of ammonium persulfate is added to the primary material, followed by stirring. Further, a reaction solution comprising 30 parts of ion-exchanged water, 0.2 part of potassium laurylsulfate, 30 parts of styrene, 15 parts of butyl methacrylate, 16 parts of butyl acrylate, 2 parts of acrylic acid, 1 part of 1,6-hexandiol dimethacrylate and 0.5 part of t-dodecylmercaptan is added with stirring at 70° C. to conduct reaction, followed by neutralization with ammonia to pH 8 to 8.5. Then, the resulting solution is filtered through a 0.3-μm filter to prepare a dispersion of tine polymer particles. This is taken as Emulsion A.

Fine Polymer Particles B:

In a reaction vessel equipped with a dropping equipment, a thermometer, a water cooled reflux condenser and a stirrer, 100 parts of ion exchanged water is placed, and 0.2 part of potassium persulfate is added as a polymerization initiator in an atmosphere of nitrogen at 70° C. with stirring. A monomer solution obtained by adding 0.05 part of sodium laurylsulfate, 10 parts of styrene, 10 parts of butyl methacrylate and 0.02 part of t-dodecylmercaptan to 7 parts of ion-exchanged water is added dropwise to the resulting aqueous solution at 70° C. to conduct reaction, thereby preparing a primary material. Then, 2 parts of a 10% solution of ammonium persulfate is added to the primary material, followed by stirring. Further, a reaction solution comprising 30 parts of ion-exchanged water, 0.2 part of potassium laurylsulfate, 35 parts of styrene, 25 parts of butyl methacrylate, 10 parts of acrylic acid, 1 part of bisphenol A dimethacrylate and 0.5 part of t-dodecylmercaptan is added with stirring at 70° C. to conduct reaction, followed by neutralization with ammonia to pH 8 to 8.5. Then, the resulting solution is filtered through a 0.3-nm filter to prepare a dispersion of fine polymer particles. This is taken as Emulsion B.

Fine Polymer Particles C:

In a reaction vessel equipped with a dropping equipment, a thermometer, a water cooled reflux condenser and a stirrer, 100 parts of ion-exchanged water is placed, and 0.2 part of potassium persulfate is added as a polymerization initiator in an atmosphere of nitrogen at 70° C. with stirring, h monomer solution obtained by adding 0.05 part of sodium laurylsulfate, 15 parts of styrene, 6 parts of benzyl methacrylate, 10 parts of butyl methacrylate and 0.02 part of t-dodecylmercaptan to 7 parts of ion-exchanged water is added dropwise to the resulting aqueous solution at 70° C. to conduct reaction, thereby preparing a primary material. Then, 2 parts of a 10% solution of ammonium persulfate is added to the primary material, followed by stirring. Further, a reaction solution comprising 30 parts of ion-exchanged water, 0.2 part of potassium laurylsulfate, 30 parts of styrene, 15 parts of butyl methacrylate, 10 parts of acrylic acid, 1 part of triethanolpropane trimethacrylate, 1 part of 1,6-hexandiol dimethacrylate and 0.5 part of t-dodecylmercaptan is added with stirring at 70° C. to conduct reaction, followed by neutralization with ammonia to pH 8 to 8.5. Then, the resulting solution is filtered through a 0.3-μm tilter to prepare a dispersion of fine polymer particles. This is taken as Emulsion C.

Fine Polymer Particles D:

In a reaction vessel equipped with a dropping equipment, a thermometer, a water cooled reflux condenser and a stirrer, 100 parts of ion-exchanged water is placed, and 0.2 part of potassium persulfate is added as a polymerization initiator in an atmosphere of nitrogen at 70° C. with stirring. A monomer solution obtained by adding 0.05 part of sodium laurylsulfate, 15 parts of styrene, 15 parts of butyl methacrylate and 0.02 part of t dodecylmercaptan to 7 parts of ion-exchanged water is added dropwise to the resulting aqueous solution at 70° C. to conduct reaction, thereby preparing a primary material.

Then, 2 parts of a 10% solution of ammonium persulfate is added to the primary material, followed by stirring. Further, a reaction solution comprising 30 parts of ion-exchanged water, 0.2 part of potassium laurylsulfate, 30 parts of styrene, 15 parts of butyl methacrylate, 1 part of dipentaerythritol hexamethacrylate and 0.6 part of t-dodecyl mercaptan is added with stirring at 70° C. to conduct reaction, followed by neutralization with ammonia to pH 8 to 8.5. Then, the resulting solution is filtered through a 0.3-μm filter to prepare a dispersion of fine polymer particles. This is taken as Emulsion D.

Monomers for forming the fine polymer particles in the emulsions thus prepared include monofunctional monomers such as (α,2,3 or 4)-alkylstyrenes, (α,2,3 or 4)-alkoxystyrenes, 3,4-dimethylstyrene, α-phenylstyrene, divinylbenzene, vinylnaphthalene, dimethylamino (meth)acrylate, dimethylaminoethyl (meth)acrylate, dimethylaminopropyl acrylate, N,N-dimethylaminoethyl acrylate, acryloylmorpholine, N,N-dimethylacrylamide, N-isopropylacrylamide, N,N-diethylacrylamide, methyl (meth)acrylate, ethyl (meth)acrylate, propyl (meth)acrylate, ethylhexyl (meth)acrylate, other alkyl (meth)acrylates, methoxydiethylene glycol (meth)acrylate, ethoxy, propoxy or butoxy diethylene glycol, or polyethylene glycol (meth)acrylate, cyclohexyl (meth)acrylate, benzyl (meth)acrylate, phenoxyethyl (meth)acrylate, isobonyl (meth)acrylate, hydroxyalkyl (meth)acrylates, fluorine-, chlorine- or silicon-containing (meth)acrylates, (meth)acrylamide, maleic acid amide and (meth)acrylic acid, as well as styrene, tetrahydrofurfuryl acrylate and butyl amethacrylate. When the crosslinked structure is introduced, the monomers include (mono, di, tri, tetra or poly)ethylene glycol (meth)acrylate, (meth)acrylates of 1,4-butanediol, 1,5 pentanediol, 1,6-hexanediol, 1,8-octanediol and 1,10-decanediol, trimethylolpropane (meth)acrylate, glycerol (di or tri)(meth)acrylate, a (meth)acrylate of an ethylene oxide addition product of bisphenol A or F, neopentyl glycol (meth) acrylate, pentaerythritol tetra(meth)acrylate and dipentaerythritol hexa(meth)acrylate.

Emulsifier which can be used in forming such fine polymer particles include anionic surfactants, nonionic surfactants and amphoteric surfactants, as well as sodium laurylsulfate and potassium laurylsulfate. The surfactants which can be added to the above-mentioned ink can also be used.

Polymerization initiators which can be used in forming the above-mentioned fine polymer particles include hydrogen persulfate, azobisisobutyronitrile, benzoyl peroxide, dibutyl peroxide, peracetic acid, cumene hydroperoxide, t-butyl hydroxyperoxide and p-menthane hydroxyperoxide, as well as potassium persulfate and ammonium persulfate. As chain transfer agents for polymerization, there can be used n-dodecylmercaptan, n-octylmercaptan, xanthogens such as dimethylxanthogen disulfide and dilsobutylxantogen disulfide, dipentene, indene, 1,4-cyclohexadiene, dihydrofuran and xanthene, as well as t-dodecylmercaptan.

The substance represented by the above-mentioned formula (2) is prepared, for example, in the following manner.

An alkaline catalyst (for example, NaOH) is added to an alcohol (for example, isopropyl alcohol), and ethylene oxide gas and/or propylene oxide gas is introduced to conduct addition reaction. Unreacted ethylene oxide gas and/or propylene oxide gas is removed from the resulting substance, and the remaining alkali is removed to obtain a purified reaction product. The reaction product is obtained as a mixture of substances different in the binding ratio of ethylene oxide and/or propylene oxide. The average number (m) of repeating units is preferably at least 1.0 or more, and the average number (m) of repeating units of propyleneoxy groups is preferably 0.5 or more, when they exist. Of course, only the substances having the same number of repeating units can also be separately used.

The present invention will be illustrated in greater detail with reference to the following examples and comparative examples, but the invention should not be construed as being limited thereto.

Example 1

Synthesis Example 1

Use of Glucose, which is an Aldose

Specified amounts of glucose, a saccharide, and NaOH, an alkaline catalyst, were placed in a heat-resistant glass vessel, and the inside thereof was replaced by inert argon gas through a supply pipe. Then, the temperature of the reaction vessel was elevated to 110° C. to 130° C. with stirring to melt glucose. Ethylene oxide gas was gradually introduced in an amount expected to react, followed by stirring at that temperature for 4 hours. After the reaction was terminated, the resulting product was dried under vacuum for removing the remaining ethylene oxide gas. Further, for removing the remaining alkali, water was added to form an aqueous solution, which was passed through a filter paper laminated with diatomaceous earth to obtain an aqueous solution of a reaction product.

Ethylene oxide was introduced in an amount of 3.5 moles per mole of glucose, and allowed to react. On the measurement by GPC (gel permeation chromatography), the amount of unreacted glucose was 5% by weight (hereinafter indicated by %), the amount of an addition product of one ethylene oxide unit was 15%, the amount of an addition product of two ethylene oxide units was 30%, and the amount of an addition product of three or more ethylene oxide units was 50%. Unreacted glucose was separated to obtain a glucose-ethyleneoxy derivative to which 3.3 moles of ethylene oxide was added on average.

Example 2

Synthesis Example 2

Use of Erythrose, which is an Aldose

An aqueous solution of a reaction product was obtained in the same manner as with Synthesis Example 1 with the exception that the saccharide was substituted by erythrose, and the alkaline catalyst was substituted by triethanolamine.

Ethylene oxide was introduced in an amount of 2.5 moles per mole of erythrose, and allowed to react. On the measurement by GPC (gel permeation chromatography), the amount of unreacted glucose was 15%, the amount of an addition product of one ethylene oxide unit was 35%, the amount of an addition product of two ethylene oxide units was 30%, and the amount of an addition product of three or more ethylene oxide units was 20%. Unreacted erythrose was separated to obtain an erythrose-ethyleneoxy derivative to which 2.4 moles of ethylene oxide was added on average.

Example 3

Synthesis Example 3

Use of Xylulose, which is a Ketose

An aqueous solution of a reaction product was obtained in the same manner as with Synthesis Example 1 with the exception that the saccharide was substituted by xylulose, the alkaline catalyst was substituted by KOH, and the inert gas was substituted by nitrogen.

Ethylene oxide was introduced in an amount of 2.0 moles per mole of xylulose, and allowed to react. On the measurement by GPC (gel permeation chromatography), the amount of unreacted xylulose was 25%, the amount of an addition product of one ethylene oxide unit was 35%, the amount of an addition product of two ethylene oxide units was 25%, and the amount of an addition product of three or more ethylene oxide units was 15%. Unreacted xylulose was separated to obtain a xylulose-ethyleneoxy derivative to which 1.9 moles of ethylene oxide was added on average.

Example 4

Synthesis Example 4

Use of Fructose, which is a Ketose

An aqueous solution of a reaction product was obtained in the same manner as with Synthesis Example 3 with the exception that the saccharide was substituted by fructose, and the alkaline catalyst was substituted by monoethanolamine.

Ethylene oxide was introduced in an amount of 3.0 mules per mole of fructose, and allowed to react. On the measurement by GPC (gel permeation chromatography), the amount of unreacted fructose was 5%, the amount or an addition product of one ethylene oxide unit was 30%, the amount of an addition product of two ethylene oxide units was 20%, and the amount of an addition product of three or more ethylene oxide units was 45%. Unreacted fructose was separated to obtain a fructose-ethyleneoxy derivative to which 2.8 moles of ethylene oxide was added on overage.

Example 5

Synthesis Example 5

Use of Xylitol, which is a Sugar Alcohol

An aqueous solution of a reaction product was obtained in the same manner as with Synthesis Example 3 with the exception that the saccharide was substituted by xylitol, the alkaline catalyst was substituted by urea, propylene oxide was introduced in the gaseous state in place of ethylene oxide to similarly obtain a propylene oxide addition product, and then, ethylene oxide gas was further introduced to add ethylene oxide.

Propylene oxide and ethylene oxide were introduced in amounts of 1 mole and 3.0 moles, respectively, per mole of xylitol, and allowed to react. On the measurement by GPC (gel permeation chromatography), the amount of unreacted xylitol was 5%, the amount of an addition product of one propylene oxide unit was 5%, the amount of an addition product of one ethylene oxide unit was 15%, the amount of an addition product of two propylene oxide units was 5%, the amount of an addition product of two ethylene oxide units was 10%, the amount of an addition product of three or more propylene oxide units was 5%, the amount of an addition product of three or more ethylene oxide units was 20%, the amount of an addition product of one propylene oxide unit and two ethylene oxide units was 15%, the amount of an addition product of one propylene oxide unit and three or more ethylene oxide units was 10%, and the amount of an addition product of two or more propylene oxide units and one or more ethylene oxide units was 10%. Unreacted xylitol was separated to obtain a mixture of xylitol-alkyleneoxy derivatives comprising a xylitol-propyleneoxy derivative to which 1.0 mole of propylene oxide was added on average, and a xylitol-ethyleneoxy derivative to which 2.9 moles of ethylene oxide was added on average.

Example 6

Synthesis Example 6

Use of Sorbitol, which is a Sugar Alcohol

An aqueous solution of a reaction product was obtained in the same manner as with Synthesis Example 3 with the exception that the saccharide was substituted by sorbitol, and the alkaline catalyst was substituted by tripropanolamine.

Ethylene oxide was introduced in an amount of 3.0 moles per mole of sorbitol, and allowed to react. On the measurement by GPC (gel permedtion chromatography), the amount of unreacted sorbitol was 5%, the amount of an addition product of one ethylene oxide unit was 30%, the amount of an addition product of two ethylene oxide units was 20%, and the amount of an addition product of three or more ethylene oxide units was 45%. Unreacted sorbitol was separated to obtain a sorbitol-ethyleneoxy derivative to which 2.9 moles of ethylene oxide was added on average.

When the reaction products obtained as described above (the saccharide-alkyleneoxy derivatives represented by formula (1) or the mixtures thereof) are used in the ink, they may be either added in the aqueous solution state, or used in the dried state.

Examples are described in detail below in which the saccharide-alkyleneoxy derivatives represented by formula (1) or the mixtures thereof obtained as described above are added to the ink.

In the following examples, there are cases where a dye, a pigment, or both a dye and a pigment are used as water-soluble coloring material(s).

Water-soluble pigments 1 to 4 used in the following examples have structures having carbonyl groups, carboxyl groups, hydroxyl groups, sulfone groups, etc. at their ends by dispersion treatment of surfaces of carbon black particles having a size of 10 nm to 300 nm by oxidation.

Each average particle size is indicated in nm in parentheses.

Water-soluble dye 1 is Direct Black 154, water-soluble dye 2 is Direct Yellow 132, water-soluable dye 3 is Direct Blue 86, and water-soluble dye 4 is Acid Red 52.

Example 7

|  | Amount Added (wt %) |
|---|---|
| Water-Soluble Pigment 1 (95) | 5.0 |
| Substance Obtained in Example 1 | 7.0 |
| Substance (1) of Formula (2) | 3.0 |
| DEGmBE | 5.0 |
| Orfin STG | 0.8 |
| Fine Polymer Particles A | 3.0 |
| Triehtylene Glycol | 10.0 |
| Maltitol | 2.0 |
| 2-Pyrrolidone | 2.0 |
| Triethanolamine | 0.8 |
| Ion-Exchanged Water | the balance |

In substance (1) of formula (2), R is an isopentanol group, m is 5.5, and 1.5 propyleneoxy units and 4 ethyleneoxy units are added to R.
DEGmBE: Diethylene glycol monobutyl ether
Orfin STG: Acetylene glycol surfactant (manufactured by Nissin Chemical Industry Co., Ltd.)

The surface tension of the ink at 25° C. is 30 mN/m.

Example 8

|  | Amount Added (wt %) |
|---|---|
| Water-Soluble Pigment 2 (85) | 4.5 |
| Substance Obtained in Example 2 | 10.0 |
| Substance (2) of formula (2) | 1.5 |
| DPGmBE | 3.0 |
| DEGmBE | 5.0 |
| Orfin E1010 | 1.0 |
| Fine Polymer Particles A | 3.0 |
| Dipropylene Glycol | 5.0 |
| Lactosucrose | 5.0 |
| Glycerol | 2.0 |
| Surfynol 465 | 1.2 |
| Triethanolamine | 0.9 |
| Ion-Exchanged Water | the balance |

In substance (2) of formula (2), R is an isopentanol group, m is 4.5, and 1.0 propyleneoxy unit and 3.5 ethyleneoxy units are added to R.
DPGmBE: Dipropylene glycol monobutyl ether
Orfin E1010: Acetylene glycol surfactant (manufactured by Nissin Chemical Industry Co., Ltd.)
Surfynol 465: Acetylene glycol surfactant (manufactured by Air Products (U.S.A.))

The surface tension of the ink at 25° C. is 31 mN/m.

Example 9

|  | Amount Added (wt %) |
|---|---|
| Water-Soluble Pigment 3 (90) | 5.5 |
| Substance Obtained in Example 3 | 6.5 |
| PGmBE | 3.5 |
| TEGmBE | 5.0 |
| Surfynol 104 | 0.3 |
| Fine Polymer Particles B | 10.0 |
| Diethylene Glycol | 7.0 |
| Thiodiglycol | 3.5 |
| 1,6-Hexanediol | 5.0 |
| Diethylethanolamine | 1.0 |
| Potassium Hydroxide | 0.1 |
| Ion-Exchanged Water | the balance |

PGmBE: Propylene glycol monobutyl ether
TEGmBE: Tetraethylene glycol monobutyl ether
Surfynol 104: Acetylene glycol surfactant (manufactured by Air Products (U.S.A.))

The surface tension of the ink at 25° C. is 29 mN/m.

Example 10

|  | Amount Added (wt %) |
|---|---|
| Water-Soluble Pigment 4 (80) | 5.0 |
| Water-Soluble Dye 1 | 1.0 |
| Substance Obtained in example 4 | 8.0 |
| DEGmDE | 5.0 |
| TEGmBE | 5.0 |
| Fine Polymer Particles C | 1.0 |
| Glycerol | 10.0 |
| Tetraethylene Glycol | 4.0 |
| 1,5-Pentanediol | 2.0 |
| Dimethyl-2-imidazolidinone | 2.0 |
| Sodium Benzoate | 0.1 |
| Triethanolamine | 0.7 |
| Ion-Exchanged Water | the balance |

The surface tension of the ink at 25° C. is 33 mN/m.

Example 11

|  | Amount Added (wt %) |
|---|---|
| Water-Soluble Pigment 1 (105) | 3.0 |
| Water-Soluble Dye 1 | 1.0 |
| Substance Obtained in Example 5 | 4.0 |
| DEGmBE | 9.0 |
| Orfin STG | 0.3 |
| Fine Polymer Particles D | 1.0 |
| Glycerol | 10.0 |
| Triethanolamine | 0.9 |
| Ion-Exchanged Water | the balance |

The surface tension of the ink at 25° C. is 31 mN/m.

Example 12

| | Amount Added (wt %) |
|---|---|
| Water-Soluble Dye 2 | 5.0 |
| Substance Obtained in Example 6 | 5.0 |
| DPGmBE | 4.0 |
| DEGmBE | 8.0 |
| Glycerol | 15.0 |
| Thiodiglycol | 2.0 |
| 1,6-Pentanediol | 1.0 |
| Triethanolamine | 0.9 |
| Ion-Exchanged Water | the balance |

The surface tension of the ink at 25° C. is 31 mN/m.

Example 13

| | Amount Added (wt %) |
|---|---|
| Water-Soluble Dye 3 | 5.0 |
| Substance Obtained in Example 1 | 3.0 |
| Substance Obtained in Example 3 | 2.0 |
| Substance (3) of Formula (2) | 5.0 |
| Glycerol | 5.0 |
| Fructose | 5.0 |
| Trimethylolpropane | 1.0 |
| Trimethylolethane | 1.0 |
| Surfynol 465 | 1.0 |
| Triethanolamine | 0.5 |
| KOH | 0.05 |
| Ion-Exchanged Water | the balance |

In substance (3) of formula (2), R is a methyl-isobutylcarbinol group, and 1.5 propyleneoxy units and 4.5 ethyleneoxy units are added to R.

The surface tension of the ink at 25° C. is 32 mN/m.

Example 14

| | Amount Added (wt %) |
|---|---|
| Water-Soluble Dye 4 | 5.5 |
| Substance Obtained in Example 2 | 4.0 |
| Substance Obtained in Example 5 | 4.0 |
| DEGmBE | 10.0 |
| Glycerol | 5.0 |
| Diethylene Glycol | 5.0 |
| Tetrapropylene Glycol | 5.0 |
| Triethanolamine | 0.9 |
| Tripropanolamine | 0.1 |
| Ion-Exchanged Water | the balance |

The surface tension of the ink at 25° C. is 30 mN/m.

The compositions or ink used in Comparative Examples are as follows. As pigments shown in Comparative Examples, there was used carbon black dispersed with a random copolymer type styrene-acrylic acid dispensing agent. The average particle size of the pigments is indicated in nm in parentheses.

Comparative Example 1

| | Amount Added (wt %) |
|---|---|
| Water-Soluble Pigment 9 (90) | 5.0 |
| Glycerol | 10.0 |
| Styrene-Acrylic Acid Dispersing Agent | 3.0 |
| Nonionic surfactant Noigen EA160 (Dai-ichi Kogyo Seiyaku Co., Ltd.) | 1.0 |
| Ion-Exchanged Water | the balance |

Comparative Example 2

| | Amount Added (wt %) |
|---|---|
| Water-Soluble Dye (Food Black 2) | 5.5 |
| DEGmME | 7.0 |
| Diethylene Glycol | 10.0 |
| 2-Pyrrolidone | 5.0 |
| Ion-Exchanged Water | the balance |

DEGmME: Diethylene glycol monomethyl ether

Comparative Example 3

| | Amount Added (wt %) |
|---|---|
| Water-Soluble Pigment 11 (110) | 5.5 |
| Water-Soluble Dye (Food Black 2) | 2.5 |
| Diethylene Glycol | 10.0 |
| Polyethylene Glycol Octyl Phenyl Ether | 1.0 |
| Ion-Exchanged Water | the balance |

To the ion-exchanged water of Examples, for example, Proxel XL-2 supplied from Avccia Co. was used in an amount of 0.1% to 1% for preventing ink from spoiling, benzotriazole in an amount of 0.001% to 0.05% for preventing ink jet head members from corroding, and ethylenediaminetetraacetic acid disodium salt (EDTA) in an amount of 0.01% to 0.03% for reducing the influence of metallic ions in ink systems.

Alphabetic and numerical characters were printed with the ink of the above-mentioned Examples 1 to 14 and Comparative Examples 1 to 3 on the following paper of the A-4 size using an MJ-930C ink jet printer manufactured by Seiko Epson Corporation. For the resulting printed matter, blurs were evaluated by visual observation, and judged according to the following criterion:

A: very good, B: Good, C: Poor and D: very poor.

The results thereof are shown in Table 1.

The paper used for the evaluation is ordinary paper commercially available in Europe, U.S.A. and Japan, and includes Conqueror paper, Favorite paper, Mode Copy paper, Rapid Copy paper, EPSON EPP paper, Xerox 4024 paper, Xerox 10 paper, Neenha Bond paper, Ricopy 6200 paper, Yamayuri paper and Xerox R paper.

TABLE 1

|  | Example | | | | | | | | Comparative Example | | |
| --- | --- | --- | --- | --- | --- | --- | --- | --- | --- | --- | --- |
|  | 7 | 8 | 9 | 10 | 11 | 12 | 13 | 14 | 1 | 2 | 3 |
| Conqueror | A | A | A | A | A | A | A | A | C | C | C |
| Favorit | A | A | A | A | A | A | A | A | D | D | D |
| Mode Copy | A | A | A | A | A | A | A | A | C | D | D |
| Rapid Copy | A | A | A | A | A | A | A | A | C | D | D |
| EPSON EPP | A | A | A | A | A | A | A | A | C | C | D |
| Xerox P | A | A | A | A | A | A | A | A | C | D | D |
| Xerox 4024 | A | A | A | A | A | A | A | A | C | D | D |
| Xerox 10 | A | A | A | A | A | A | A | A | B | D | D |
| Neenha Bond | A | A | A | A | A | A | A | A | C | D | D |
| Ricopy 6200 | A | A | A | A | A | A | A | A | B | C | D |
| Yamayuri | A | A | A | A | A | A | A | A | D | D | D |
| Xerox R | A | A | A | A | A | A | A | A | C | D | D |

The results of Table 1 apparently indicate that the ink as used in Comparative Examples, that is to say, the ink not containing the saccharide-alkyleneoxy derivative represented by the above-mentioned formula (1) or a mixture thereof, Is poor in printing quality, and that the use of the ink of the invention results in improvement in printing quality. When the substances of formula (2) are not added in Examples 1 to 14, it is observed that blurs are increased to deteriorate printing quality more greatly than when the substances are added.

Further, it has been observed that the ink of the invention is improved in clogging when used in the ink jet recording apparatus having a head discharging the ink by response of signals by use of an electrostrictive device, by containing the ethylene oxide and/or propylene oxide-added saccharide-alkyleneoxy derivatives represented by formula (1) or the mixtures thereof. For example, when the composition of Example 7 was allowed to stand in an MJ-930C printer at 60° C. at 40% RH for 1 week, 3 or less cycles of cleaning (one of mechanisms with which Epson-made printers are usually provided, and mode for sucking a proper amount of ink for recovering clogged nozzles) restored all nozzles. On the other hand, when the saccharide-alkyleneoxy derivative represented by the above-mentioned formula (1) or a mixture thereof was not added, tour or more cycles of cleaning were required. Similar experiments using the ink of Examples 0 to 13, as well as the ink of Example 1, also gave approximately similar results.

As described above, printed images recorded using the ink of the invention are reduced in blurs to materials to be recorded such as paper, and high in quality. Further, the highly practical ink which is hard to cause clogging even when used in an ink jet recording apparatus having a head discharging the ink by response of signals by use of an electrostrictive device, that is to say, the ink suitable for ink jet recording, can be provided.

Further, many of the saccharides which have hitherto been used in the preparation of ink are powdery or solid, so that they are poor in workability because of contamination with impurities. However, the saccharide-alkyleneoxy derivatives represented by the above-mentioned formula (1) or the mixtures thereof as used in the invention are lowered in melting point and can be used in the liquid state. They also has therefore the effect of improving workability.

As described above, the saccharide-alkyleneoxy derivatives represented by the above-mentioned formula (1) of the invention or the mixtures thereof provide excellent printing quality and improvement in clogging to ink. According to the invention, the novel substances which can yield ink excellent in printing quality and improvement in clogging, particularly ink suitable for ink jet recording, can be provided.

Further, printing is possible without blurs on plain paper which has previously been insufficient, particularly on regenerated paper, by adding the saccharide-alkyleneoxy derivatives represented by the above-mentioned formula (1) of the invention or the mixtures thereof. The invention has the excellent effect of being able to provide the ink which is hard to cause clogging, particularly the ink for ink jet recording which is hard to cause clogging even at a head tip of an ink jet recording apparatus.

While the invention has been described in detail and with reference to specific examples thereof, it will be apparent to one skilled in the art that various changes and modifications can be made therein without departing from the spirit and scope thereof.

What is claimed is:

1. Ink containing at least a coloring material, water, and a saccharide-alkyleneoxy derivative comprising a compound represented by the following formula (1):

$$A\text{-}(EP)n\text{-}OH \tag{1}$$

wherein A represents a skeleton of a saccharide selected from the group consisting of $C_3$ to $C_{12}$ aldoses, ketoses and sugar alcohols; EP represents an ethyleneoxy group and/or a propyleneoxy group; and n represents an average number of the repeating units, said ink further containing one or more $C_3$ to $C_{12}$ saccharides selected from the group consisting of: aldoses having 6 or fewer carbon atoms, aldoses having from 7 to 12 carbon atoms; ketoses having 6 or fewer carbon atoms, ketoses having from 7 to 12 carbon atoms; sugar alcohols having from 6 or fewer carbon atoms, and sugar alcohols having from 7 to 12 carbon atoms, wherein the compound represented by formula (1) is a sorbitol-ethyleneoxy compound and is present in the ink in an amount of from 4 to 10% by weight, wherein the ink contains at least one glycol ether selected from the group consisting of 5% to 20% by weight of diethylene glycol monobutyl ether, 5% to 20% by weight of triethylene glycol monobutyl ether, 3% to 10% by weight of dipropylene glycol monobutyl ether and 3.5% to 10% by weight of propylene glycol monobutyl ether, each based on the weight of said ink, wherein the ink also contains 3% to 10% by weight of 1,2-pentanediol or 0.5% to 5% by weight of 1,2-hexanediol, and wherein the coloring material is a water-soluble pigment that is made water-dispersible.

2. The ink according to claim 1, wherein the average number (n) of repeating units in said formula (1) is from 0.5 to 10.

3. The ink according to claim 1, wherein said saccharide-alkyleneoxy derivative has a molecular weight distribution of 2 or more.

4. The ink according to claim 1, wherein said saccharide-alkyleneoxy derivative has a number average molecular weight of 1000 or less.

5. The ink according to claim 1, wherein A in said formula (1) is a skeleton of a saccharide selected from the group consisting of: aldoses having 6 or fewer carbon atoms, aldoses having from 7 to 12 carbon atoms, keloses having 6 or fewer carbon atoms, sugar alcohols having 6 or fewer carbon atoms, and sugar alcohols having from 7 to 12 carbon atoms.

6. The ink according to claim 1, wherein said saccharide-alkyleneoxy derivative represented by formula (1) and said $C_3$ to $C_{12}$ saccharides are present, in total, in an amount of from 0.5% to 30% by weight based on the weight of said ink.

7. The ink according to claim 1, wherein said ink has a surface tension at 25° C. of 40 mN/m or less.

8. The ink according to claim 1, containing an acetylene glycol surfactant in an amount of 0% to 5% by weight based on the weight of said ink.

9. The ink according to claim 1, containing at least one substance represented by formula (2) below in an amount of 0% to 10% by weight based on the weight of said ink:

R-(EP)$m$-OH  (2)

wherein R represents an alkyl group having from 4 to 10 carbon atoms, which may be branched, a cycloalkyl group or a phenyl group; EP represents an ethyleneoxy group and/or a propyleneoxy group; and m represents an average number of the repeating units.

10. The ink according to claim 9, wherein the average number (m) of the repeating units in the substance represented by said formula (2) is from 1 to 10 and, when propyleneoxy groups represented by EP exist, the average number of repeating units of propyleneoxy groups is from 0.5 to 5.

11. The ink according to claim 1, wherein said pigment is made water dispersible by at least one of surface oxidation and coating with a polymer.

12. A method for jet recording comprising providing the ink according to claim 1, and ejecting the ink onto a recording medium.

13. A method for ink jet recording comprising providing the ink according to claim 1 and ejecting said ink from an ink jet recording apparatus having a head which discharges the ink in response to a signal using an electrostrictive device.

14. The ink according to claim 1, wherein the one or more $C_3$ to $C_{12}$ saccharides comprise glycerol.

15. The ink according to claim 1, wherein the one or more $C_3$ to $C_{12}$ saccharides are present in the ink in an amount of from 3-15 wt %.

16. Ink containing at least a coloring material, water, and a saccharide-alkyleneoxy derivative comprising a compound represented by the following formula (1):

A-(EP)$n$-OH  (1)

wherein A represents a skeleton of a saccharide selected from the group consisting of $C_3$ to $C_{12}$ aldoses, ketoses and sugar alcohols; EP represents an ethyleneoxy group and/or a propyleneoxy group; and n represents an average number of the repeating units, said ink further containing one or more $C_3$ to $C_{12}$ saccharides selected from the group consisting of: aldoses having 6 or fewer carbon atoms, aldoses having from 7 to 12 carbon atoms; ketoses having 6 or fewer carbon atoms, ketoses having from 7 to 12 carbon atoms; sugar alcohols having from 6 or fewer carbon atoms, and sugar alcohols having from 7 to 12 carbon atoms, wherein the compound represented by formula (1) is present in the ink in an amount of from 4 to 10% by weight, wherein the ink contains at least one glycol ether selected from the group consisting of 5% to 20% by weight of diethylene glycol monobutyl ether, 5% to 20% by weight of triethylene glycol monobutyl ether, 3% to 10% by weight of dipropylene glycol monobutyl ether and 3.5% to 10% by weight of propylene glycol monobutyl ether, each based on the weight of said ink, wherein the ink also contains 3% to 10% by weight of 1,2-pentanediol or 0.5% to 5% by weight of 1,2-hexanediol, wherein the coloring material is a water-soluble pigment that is made water-dispersible, and wherein the pigment is dispersed in the ink without a dispersing agent.

17. The ink according to claim 16, wherein the pigment is a surface-treated pigment or a pigment coated with a polymer and the compound of formula (I) is a sorbitol-ethyeneoxy compound.

18. The ink according to claim 16, containing an acetylene glycol surfactant in an amount effective to reduce blur of an image formed with the ink on a recording medium comprising paper, said amount being up to 5% by weight based on the weight of the ink.

* * * * *